(12) United States Patent
Peach

(10) Patent No.: US 8,702,945 B2
(45) Date of Patent: *Apr. 22, 2014

(54) TIME-VARYING FLOWS FOR MICROFLUIDIC PARTICLE SEPARATION

(75) Inventor: Joseph Edward Tucker Peach, Seattle, WA (US)

(73) Assignee: University of Washington, Seattle, WA (US)

( * ) Notice: Subject to any disclaimer, the term of this patent is extended or adjusted under 35 U.S.C. 154(b) by 1280 days.

This patent is subject to a terminal disclaimer.

(21) Appl. No.: 12/122,577

(22) Filed: May 16, 2008

(65) Prior Publication Data

US 2008/0283401 A1    Nov. 20, 2008

Related U.S. Application Data

(60) Provisional application No. 60/938,826, filed on May 18, 2007.

(51) Int. Cl.
*G01N 27/26* (2006.01)
*B01D 57/02* (2006.01)

(52) U.S. Cl.
USPC ........ 204/547; 204/643; 204/600; 435/287.1; 422/68.1; 422/82.01

(58) Field of Classification Search
USPC ................. 204/463, 547, 400, 450, 600–647; 422/68.1, 82.01; 435/287.1
See application file for complete search history.

(56) References Cited

U.S. PATENT DOCUMENTS

| | | | |
|---|---|---|---|
| 5,040,560 A | 8/1991 | Glezer | |
| 5,454,472 A | 10/1995 | Benecke | |
| 5,569,367 A | 10/1996 | Betts | |
| 5,814,200 A | 9/1998 | Pethig | |
| 5,888,370 A * | 3/1999 | Becker et al. | 204/643 |
| 5,993,630 A | 11/1999 | Becker | |
| 5,993,632 A | 11/1999 | Becker | |
| 6,287,832 B1 | 9/2001 | Becker | |
| 6,596,143 B1 * | 7/2003 | Wang et al. | 204/547 |
| 6,641,708 B1 | 11/2003 | Becker | |
| 6,692,627 B1 | 2/2004 | Russell | |
| 6,727,451 B1 | 4/2004 | Fuhr | |
| 6,730,204 B2 | 5/2004 | Mariella, Jr. | |
| 6,749,736 B1 | 6/2004 | Fuhr | |
| 6,881,314 B1 | 4/2005 | Wang | |
| 7,029,564 B1 * | 4/2006 | Lock et al. | 204/643 |
| 7,070,684 B1 | 7/2006 | Fuhr | |
| 7,157,274 B2 | 1/2007 | Bohm | |
| 7,258,774 B2 | 8/2007 | Chou | |
| 2002/0036142 A1 * | 3/2002 | Gascoyne et al. | 204/547 |
| 2003/0159932 A1 * | 8/2003 | Betts et al. | 204/547 |
| 2004/0028559 A1 * | 2/2004 | Schuck | 422/68.1 |
| 2006/0177815 A1 | 8/2006 | Soh | |

OTHER PUBLICATIONS

Chou et al. (Biophysical Journal vol. 83 Oct. 2002 2170-2179).*
Schonfeld et al. (JALA, vol. 7, No. 6, Dec. 2002).*

(Continued)

*Primary Examiner* — Jennifer Dieterle
(74) *Attorney, Agent, or Firm* — Christensen O'Connor Johnson Kindness PLLC

(57) ABSTRACT

Methods, devices, and systems for separating a time-varying flow of disparate liquid-suspended particles through a channel using dielectrophoresis and field-flow fractionation.

12 Claims, 9 Drawing Sheets

(56) References Cited

OTHER PUBLICATIONS

Choi, S., and J.-K. Park, "Microfluidic System for Dielectrophoretic Separation Based on a Trapezoidal Electrode Array," Lab on a Chip 5(10):1161-1167, Oct. 2005 (epublished Aug. 2005).

Kralj, J.G., et al., "Continuous Dielectrophoretic Size-Based Particle Sorting," Analytical Chemistry 78(14):5019-5025, Jul. 2006.

Lao, A.I.K., and I.-M. Hsing, "Flow-Based and Sieving Matrix-Free DNA Differentiation by a Miniaturized Field Flow Fractionation Device," Lab on a Chip 5(6):687-690, Jun. 2005 (epublished Apr. 2005).

Lao, A.L.K., et al., "Mechanistic Investigation of Nanoparticle Motion in Pulsed Voltage Miniaturized Electrical Field Flow Fractionation Device by In Situ Fluorescence Imaging," Analytical Chemistry 76:2719-2724, May 2004.

Li, Y., et al., "Continuous Dielectrophoretic Cell Separation Microfluidic Device," Lab on a Chip 7(2):239-248, Feb. 2007 (epublished Dec. 2006).

Müller, T., et al., "Microdevice for Cell and Particle Separation Using Dielectrophoretic Field-Flow Fractionation," Journal of Liquid Chromatography & Related Technologies 23(1):47-59, Jan. 2000.

Park, J., et al., "An Efficient Cell Separation System Using 3D-Asymmetric Microelectrodes," Lab on a Chip 5(11):1264-1270, Nov. 2005 (epublished Sep. 2006).

Wang, X.-B., et al., "Cell Separation by Dielectrophoretic Field-Flow-Fractionation," Analytical Chemistry 72(4):832-839, Feb. 2000.

Washizu, M., et al., "Molecular Dielectrophoresis of Biopolymers," IEEE Transactions on Industry Applications 30(4):835-843, Jul./Aug. 1994.

Yang, J., et al., "Differential Analysis of Human Leukocytes by Dielectrophoretic Field-Flow-Fractionation," Biophysical Journal 78(5):2680-2689, May 2000.

Yu, C., et al. "A Three-Dimensional Dielectrophoretic Particle Focusing Channel for Microcytometry Applications," Journal of Microelectromechanical Systems 14(3):480-487, Jun. 2005.

* cited by examiner

TIME-VARYING FLOWS FOR MICROFLUIDIC PARTICLE SEPARATION

CROSS-REFERENCE TO RELATED APPLICATION

This application claims the benefit of U.S. Provisional Application No. 60/938,826, filed May 18, 2007, expressly incorporated herein by reference in its entirety.

BACKGROUND OF THE INVENTION

DNA separation plays a critical role in many genome projects, as well as in biochemistry and microbiology. However, conventional approaches for separation of DNA (e.g., gel electrophoresis) often require large reagent volumes, time-consuming manual preparation of the experimental setup, and long run times. For large DNA molecules, the standard separation method, pulsed-field gel electrophoresis (PFGE), is time consuming with analysis times ranging from hours to days. The technique also does not accommodate continuous flow in microfluidic devices because the gel sieving matrix must be replaced after separation. Other approaches to large DNA separation involve entropic trapping and tailored geometrically-structured micro devices, but the ease of application and obtainable separation resolution of these devices has not been tested, and it is questionable whether such techniques will be commercially viable.

Separation techniques have evolved to allow for the distinction and analysis of micro- and nanoscale particles such as nucleic acids, cells, viruses, and proteins. Microfluidic separation devices have utilized dielectrophoresis (DEP), field-flow fractionation (FFF), and combinations of the two (DEP-FFF). DEP refers to the phenomenon wherein subjecting a dielectric particle to a spatially non-uniform electric field will exert a force on the particle. DEP can be used to separate particles by taking advantage of the translational motion of a particle as a result of polarization induced by a non-uniform electric field. FFF involves selectively positioning particles in a liquid having a velocity profile to increase the separation of the particles as they travel downstream. Combined DEP-FFF involves using dielectrophoresis to position particles in a flow stream having a velocity profile.

Current microfluidic devices that use DEP and/or FFF are limited in performance by a reliance on gravitational effects for separation, a lack of sufficient interaction time to properly effect separation, and difficulty in separating complex mixtures having three or more components. Further improvements on current microfluidic separation techniques are desirable to allow for faster, more accurate, and more complex analysis of mixtures of particles.

SUMMARY OF THE INVENTION

The invention provides methods, devices, and systems for manipulating particles suspended in a liquid.

In one aspect, a method is provided for spatially sorting particles using dielectrophoresis and field-flow fractionation comprising the steps:

providing a channel;

providing a first plurality of electrodes extending into the channel, and a second plurality of electrodes extending into the channel;

applying a first voltage to the first plurality of electrodes and a second voltage to the second plurality of electrodes such that the first plurality of electrodes is at a different electric potential than the second plurality of electrodes; and moving a liquid at a time-varying flow rate through the channel, the liquid having a first plurality of particles suspended therein and a second plurality of particles suspended therein, wherein the first plurality of particles and the second plurality of particles each have a property that affects dielectrophoretic forces induced by the applied first and second voltages, wherein the property is different in the first plurality of particles than in the second plurality of particles such that the first plurality of particles are urged laterally away from the second plurality of particles; thereby separating the first plurality of particles longitudinally from the second plurality of particles with field-flow fractionation from the liquid lateral velocity profile.

In another aspect, a device is provided for spatially sorting particles suspended in a liquid, comprising:

a channel;

a first plurality of electrodes extending into the channel, and a second plurality of electrodes extending into the channel;

an electrical power source operatively connected to the array of electrodes, and operable to apply a first voltage to the first plurality of electrodes and a second voltage to the second plurality of electrodes such that the first plurality of electrodes is at a different electric potential than the second plurality of electrodes; and a means for flowing a liquid through the channel in a time-varying manner, the liquid having a plurality of disparate particles suspended therein; such that the disparate particles suspended in the liquid are subjected to a non-uniform electrical field, thereby providing a lateral dielectrophoretic force on the disparate particles, wherein the disparate particles are laterally separated by the lateral dielectrophoretic force and longitudinally separated by field-flow fractionation from the liquid lateral velocity profile.

In another aspect, a system is provided for spatially sorting particles suspended in a liquid, comprising a channel;

a first plurality of electrodes extending into the channel, and a second plurality of electrodes extending into the channel;

an electrical power source operatively connected to the array of electrodes, and operable to apply a voltage to the first plurality and second plurality of electrodes such that the first plurality of electrodes is at a different electric potential than the second plurality of electrodes; and a liquid having a plurality of disparate particles suspended therein; and a means for flowing the liquid through the channel in an time-variant manner; such that the disparate particles suspended in the liquid are subjected to a non-uniform electrical field, thereby providing a lateral dielectrophoretic force on the disparate particles, wherein the particles are longitudinally separated by field-flow fractionation from the liquid lateral velocity profile.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1A:
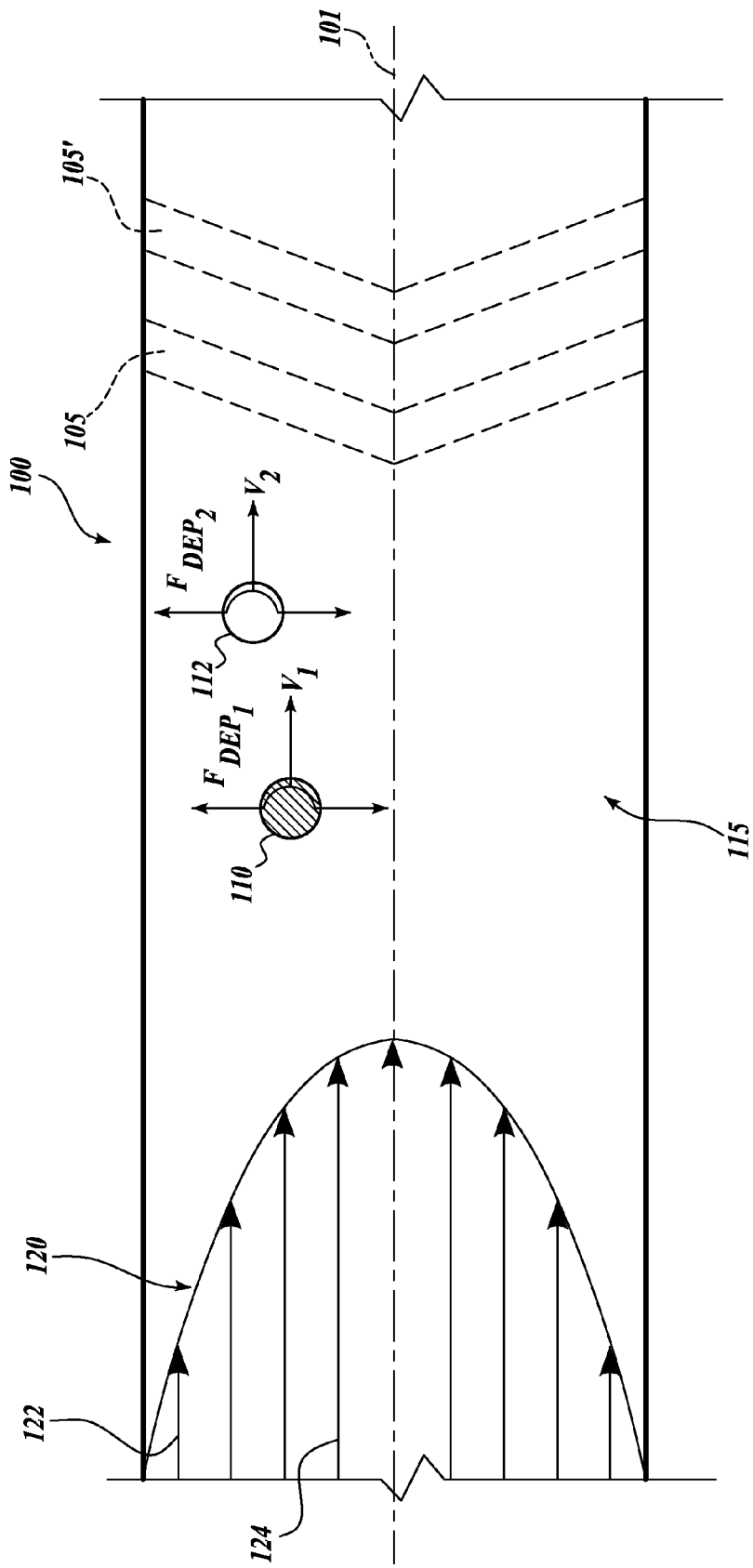
FIG. 1A is a plan-view sketch of a channel portion of a representative device in accordance with the present invention.

The invention provides methods, devices, and systems for manipulating particles suspended in a liquid.

In one aspect, a method for spatially sorting particles using dielectrophoresis and field-flow fractionation is provided. The method includes the steps of:

providing a channel having a first side and a second side;

providing a first plurality of electrodes extending into the channel, and a second plurality of electrodes interdigitated with the first plurality of electrodes and extending into the channel, the first plurality and second plurality of electrodes being disposed on one of the first side and the second side of the channel, and further wherein the first plurality and second plurality of electrodes are concave-shaped and substantially symmetric about a center line of the channel;

applying a voltage to the first plurality and second plurality of electrodes such that the first plurality of electrodes is at a different electric potential than the second plurality of electrodes; and moving a liquid having a first plurality of particles suspended therein and a second plurality of particles suspended therein through the channel, wherein the first plurality of particles and the second plurality of particles each have a property that affects induced dielectrophoretic forces, wherein the property is different in each of the pluralities of particles such that the first plurality of particles and the second plurality of particles become sorted by the property in a lateral direction as the liquid moves through the channel; thereby separating the sorted particles longitudinally with field-flow fractionation from the liquid lateral velocity profile.

Dielectrophoresis

The principle behind dielectrophoresis (DEP) lies in controlling the movement of one or more particles (e.g., DNA molecule) through the induced polarization of the particles with a non-uniform electric field, wherein a DEP force either pulls or pushes the particles toward or away from regions of highest electric field. The non-uniform electric field is typically generated using an array of electrodes. Because the direction of the DEP force does not change when the electric field is reversed, alternating voltages may be used to generate the DEP force. Using alternating signals, higher voltages can be applied without bubble formation because electrolysis is minimized at frequencies above 1 kHz. Additionally, controlling the frequency of the electric field provides the ability to induce either positive DEP (force towards high electric field) or negative DEP (force away from high electric field). The use of phase differences between electrodes allows the generation of traveling-wave DEP (TW-DEP) forces that provide additional benefits and flexibility for device functionality.

DEP is useful in the present invention for separating particles (e.g., separating DNA molecules by length) and generally sorting particles, including nucleic acids, cells, nanotubes (e.g., carbon nanotubes), and viruses, by any property that influences the dielectrophoretic force (e.g., size or composition) and movement of the particles in a liquid.

The force exerted on a particle by DEP can be estimated for a spherical particle in an electric field E, based on Equation 1, wherein $F_{DEP}$ is the DEP force; r is the radius of the particle; $\epsilon_0$ is the permittivity of free space; $\epsilon_m$ is the permittivity of the medium; and Re[K] is the real part of the Clausius-Mossotti factor K described in Equation 2, wherein $\epsilon_p^*$ and $\epsilon_m^*$ are the complex permittivities of the particle and the medium, respectively.

$$F_{DEP} = 2\pi r^3 \epsilon_0 \epsilon_m \text{Re}[K] \nabla |E(x, y)|^2 \quad (1)$$

$$K = \frac{\epsilon_p^* - \epsilon_m^*}{\epsilon_p^* + 2\epsilon_m^*} \quad (2)$$

Complex permittivity is described by Equation 3, wherein $\epsilon$ is the permittivity, $\sigma$ is the electrical conductivity, and $\omega$ is the electric field frequency.

$$\epsilon^* = \epsilon - i\frac{\sigma}{\omega} \quad (3)$$

Because the complex permittivity is affected by the frequency of the electric field, the value of K (and therefore $F_{DEP}$) can be positive or negative. When Re[K] is positive, the DEP force is classified as positive DEP and the force is in the direction of higher electric field. When Re[K] is negative, negative DEP occurs and the force is in the direction away from higher electric field. Thus, the DEP force can be attractive or repulsive based on the frequency of the applied electric field. According to Equations 1-3, the size of the particle and its dielectric properties contribute to the magnitude of $F_{DEP}$. Additionally, the value of $F_{DEP}$ depends on the medium.

As discussed above, the electric field frequency can determine if a particle is repelled away from or urged towards regions of high electric field. Typical particles will have a crossover frequency where a transition is made from positive DEP to negative DEP. Particles of similar composition and different size can be separated using a frequency between the crossover frequencies of the two particles because the DEP force will push the different particles in different directions. The practical result is that by judicious selection of the electric-field frequency, one particle type may be urged toward the edges of the channel while another particle type is urged towards the center of the channel.

DEP can be used in two different ways, which are not mutually exclusive. First, DEP can deflect particles traveling near electrodes. For example, a particle that is affected by the DEP force may travel along a high electric field region created by V-shaped electrodes. Lateral movement of a population of particles can occur because the DEP force acts to trap particles in the high electric field region while the hydrodynamic (drag) force pushes the particles in the direction of the flow. In an exemplary embodiment, this "shunting" occurs when the fluid containing particles flows in the direction from the points of V-shaped electrodes towards the legs of the V-shaped electrodes. The result is typically a lateral movement of particles strongly affected by the DEP force towards the edges of the channel as the affected particles are retained near the edges of the V-shaped electrodes by the DEP force but move downstream along the legs of the V-shaped electrodes due to hydrodynamic force. Separation of disparate particles can be accomplished if a DEP force and flow rate are selected that affects one type of particle but does not affect or differently affects a second type of particle. The affected particles are moved towards the edges and the unaffected particles are not laterally moved in the channel. Field-flow fractionation then longitudinally separates particles at the edges from particles nearer the center of the channel.

In a second embodiment, the DEP force is used to push or pull particles laterally in a channel. In an illustrative embodiment of the push/pull DEP mechanism, two particles of similar material that have different radii are separated laterally by bowtie-shaped electrodes. If the electrodes exert a negative DEP force on the larger particles and a positive DEP force on the smaller particles, the smaller particles will be pulled to the highest electric field region created by the electrode and the larger particles will be pushed away from these regions. Thus, lateral separation is induced based on push/pull DEP.

As discussed above, field-flow fractionation uses a liquid velocity profile to separate particles. For example, in parabolic flow in a channel, the liquid velocity profile across the channel will carry particles in higher-velocity regions (near the center of the channel) further than those that are trapped in lower-velocity regions (near the edges of the channel). In a representative device that sorts DNA using DEP-FFF, when DNA is carried past the electrodes in the channel, the DEP force acts more strongly on larger DNA strands. Larger DNA molecules may be deflected to a larger degree than smaller DNA molecules by the high electric field gradient regions near the edges of the electrodes. As a result, larger DNA molecules may be preferentially pushed towards the edges of the channel where liquid velocities are relatively low and therefore take longer to flow through the channel.

FIG. 1A is a schematic illustration showing a plan view of a longitudinal channel 100 having a centerline 101. A liquid 115 containing a plurality of particles, represented by particles 110, 112, streams through the channel 100. The particles 110, 112 are manipulated by a DEP force generated by an electric field generated using spaced electrodes 105, 105' (shown in phantom) such that the DEP forces, $F_{DEP1}$ and $F_{DEP2}$ urge the particles 110, 112 towards different locations in the channel 100. As a result of the positioning of the particles 110, 112 through the DEP forces, the particles 110, 112 are subject to different liquid-flow velocities in the channel 100. $V_1$ and $V_2$ represent the velocities of the individual particles 110, 112, respectively, in the liquid 115. A typical parabolic hydrodynamic velocity profile 120 is shown for a vertically-centered portion of the channel 100, wherein the size of the arrows in the velocity profile 120 represent the local liquid velocities 122, 124 of the liquid 115. The effect of the velocity profile 120 on the particles 110, 112 results in field-flow fractionation wherein particle 110 (closer to the channel centerline 101 and thus liquid velocity 124) is transported with a higher velocity than particle 112 (closer to liquid velocity 122).

Figure 1B:
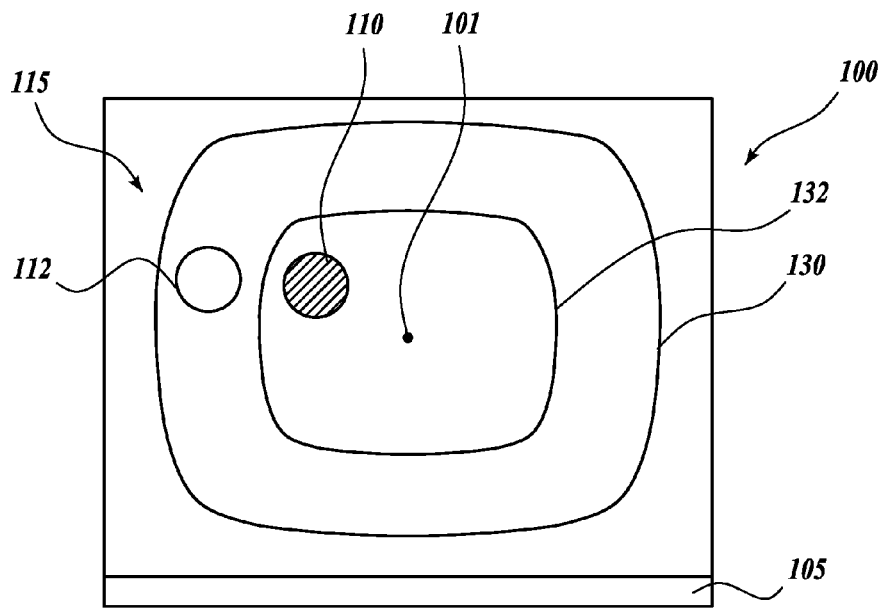
FIGS. 1B-1C are front cross-sectional sketches of the channel shown in FIG. 1A.

FIG. 1B illustrates a front cross-sectional view of the channel 100 illustrated in FIG. 1A. In the representative device configuration illustrated in FIG. 1B, the electrodes 105 (105' not pictured) are disposed on the bottom surface of the channel 100. Iso-velocity contours 130, 132 graphically indicate uniform velocity contours in the liquid 115. The liquid 115 flows faster closer to the centerline 101, thus particle 110, situated inwardly of iso-velocity flow line 132, flows faster through the channel 100 than particle 112, situated between flow lines 130 and 132.

Figure 1C:
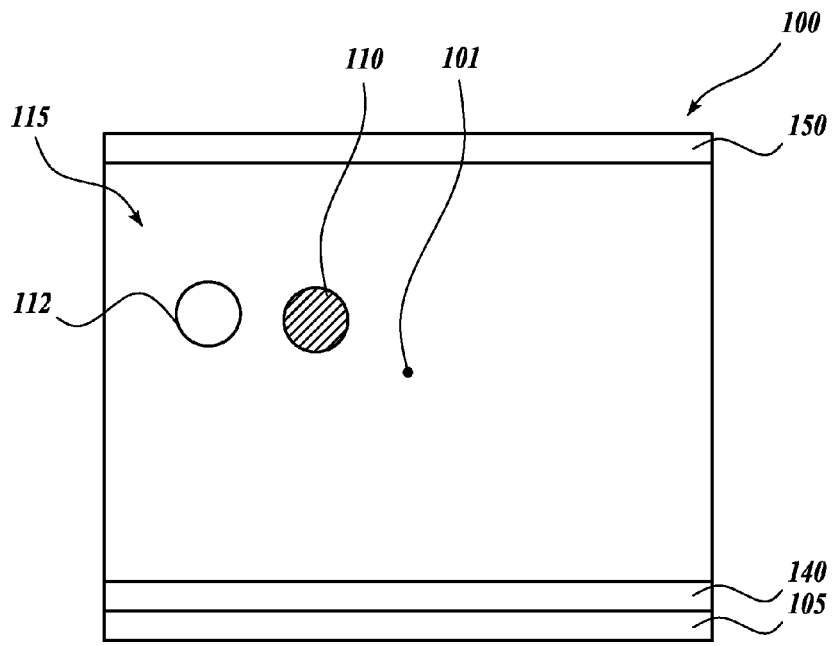

FIG. 1C illustrates two optional features useful in the channel 100. First, a protective layer 140 can be used to protect the electrodes 105 (105' not pictured) from exposure to the liquid 115 if detrimental effects (e.g., oxidation) are possible. The electric field can also be selectively modified by adding the protective layer 140. Second, it is contemplated that additional electrodes 150 may be provided to further shape the electric field in the channel 100. While the additional electrodes can be located on any surface in the channel 100, top surface electrodes 150 are illustrated in FIG. 1C.

Devices

In another aspect, devices are provided for spatially sorting particles suspended in a liquid having:

(a) a channel having a first side and a second side;

(b) an array of electrodes comprising a first plurality of electrodes extending into the channel and a second plurality of electrodes interdigitated with the first plurality of electrodes and extending into the channel, the first and second plurality of electrodes being disposed on the first side of the channel, and further wherein the electrodes are concave-shaped and substantially symmetric about a center line of the channel;

(c) an electrical power source operatively connected to the array of electrodes, and operable to apply a voltage to the first plurality and second plurality of electrodes such that the first plurality of electrodes is at a different electric potential than the second plurality of electrodes; and (d) a means for flowing a liquid through the channel, the liquid having a plurality of disparate particles suspended therein; such that the disparate particles suspended in the liquid are subjected to a non-uniform electrical field, thereby providing a lateral dielectrophoretic force on the disparate particles, wherein the particles are longitudinally separated by field-flow fractionation from the liquid lateral velocity profile.

Devices of the invention may be used, for example, to sort particles (e.g., 110, 112) through lateral and vertical deflections induced by DEP. The electrodes 105, 105' generate non-uniform electric fields in the channel 100. DEP forces act on the particles 110, 112, as they travel through the channel 100.

Figure 2A:
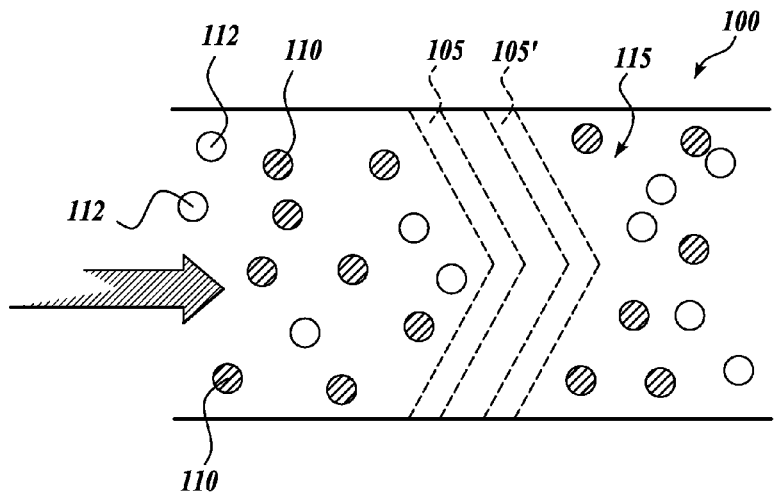
FIGS. 2A-2C illustrate the operation of a representative device in accordance with the present invention.
Figure 2B:
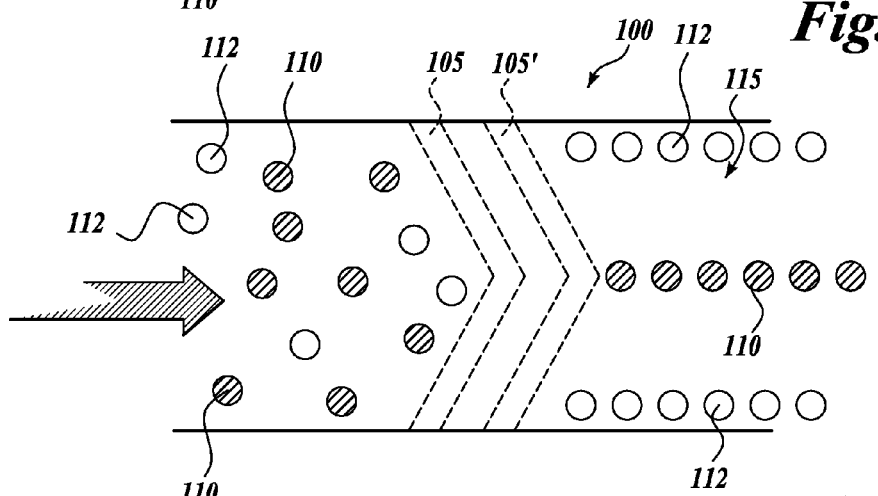
Figure 2C:
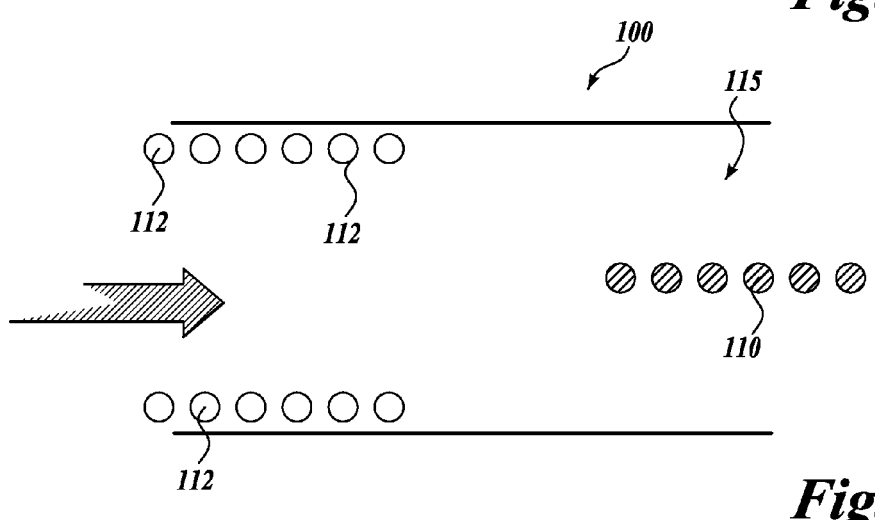

Exemplary device operation is illustrated in plan view in FIGS. 2A-2C, where the liquid 115 flows through the channel 100 in the direction of the arrow (from left to right). In FIG. 2A, the liquid 115 contains particles 110, 112 having disparate properties (e.g., size, composition). Two electrodes 105, 105' (shown in phantom) are disposed on the bottom of the channel 100. In FIG. 2A, no electrical signal is applied to the electrodes 105, 105' and the particles 110, 112 have a random distribution throughout the channel 100.

An electric field is applied across the electrodes 105, 105' in FIG. 2B, generating a non-uniform electric field in the channel 100. The effect of the field on the particles 110, 112 is a DEP force that, in this idealized example, urges a first plurality of particles 110 towards the center of the channel 100 and urges a second plurality of particles 112 towards the sides of the channel 100. In addition to being laterally urged by the DEP force, the particles 110, 112 may also be urged vertically (out of the plane of the figure).

FIG. 2C shows the channel 100 downstream of the electrodes 105, 105' and illustrates the results of longitudinal separation from field-flow fractionation. The lateral (and vertical) separation of particles 110, 112 and field-flow fractionation results in particles having disparate properties arriving at the end of the channel 100 at distinct times and in distinct populations (e.g., the first plurality of particles 110 arrives at the terminus of the channel 100 before the second plurality of particles 112).

Representative devices have multiple arrays of interdigitated electrodes 105, 105'. The shape, spacing, electric driving voltage and frequency, and number of electrodes per array can be varied to produce particular DEP-FFF separation effects. Variations in the devices can be made for a particular system of particles (e.g., 110, 112) and liquid 115 because the properties of the particles (e.g., permittivity, size) and liquid 115 (e.g., permittivity) that influence the DEP force are determined for each particle/liquid system and the electric field necessary to perform the desired separation is determined based on the properties of the particles and liquid.

In one embodiment, the channel 100 is from 5 to 5000 microns wide. In one embodiment, the channel is from 20 to 100 microns wide. In one embodiment, channel has a cross-sectional area of from 5 to 50,000 microns$^2$.

Electrodes

The preferred electrodes are concave. As used herein, the term "concave" refers to electrodes where the portion of the electrode that extends into the channel has a non-linear shape that forms a curved or segmented concave shape across the longitudinal dimension of the channel 100. Representative concave shapes include V-shaped electrodes, where the point of the V can be sharp or rounded; arcuate; and bowtie-shaped electrodes. Electrodes are typically in arrays that consist of at least two interdigitated pluralities of electrodes. A device may contain several arrays of electrodes, wherein the arrays can be the same or different. Electrodes and arrays can be individually connected to a voltage source or pluralities of electrodes can be connected by buses that provide a monolithic unified contact for multiple electrodes.

Electrodes that are substantially symmetric about a channel centerline 101 are preferred. Representative devices utilize DEP as either a centering or anti-centering force. Symmetric electrodes 105, 105' are useful for producing both strong electric fields along the centerline 101 of the channel and symmetric electric field strengths disposed laterally from the centerline 101 to the left and right sides of the channel 100. The symmetric electric fields created on both sides of the centerline 101 result in consistent sorting of disparate particles (e.g., 110, 112) both laterally and vertically in the channel 100. Consistent sorting of particles 110, 112 laterally and vertically results in similar particles being affected uniformly by field-flow fractionation (even if on opposite sides of the centerline 101) and thus longitudinal separation of disparate particles is improved by the symmetric electrodes 105, 105'.

Representative electrode configurations are illustrated in FIGS. 3A-3E. The electrode structure 105, 105' illustrated in FIG. 3A can be disposed on either the top or bottom surface of the channel 100. Also illustrated are electrode buses 106, 106' for providing a unified electrical contact for each set of electrodes 105, 105' in a binary array of electrodes. The V-shaped portion of the electrodes 105, 105' extending into the channel 100 create a non-uniform electric field as the result of the application of a voltage to the two buses 106, 106' connecting the interdigitated electrodes 105, 105'. DEP forces act on the particles as they flow past the electrodes 105, 105'.

Figure 3A:
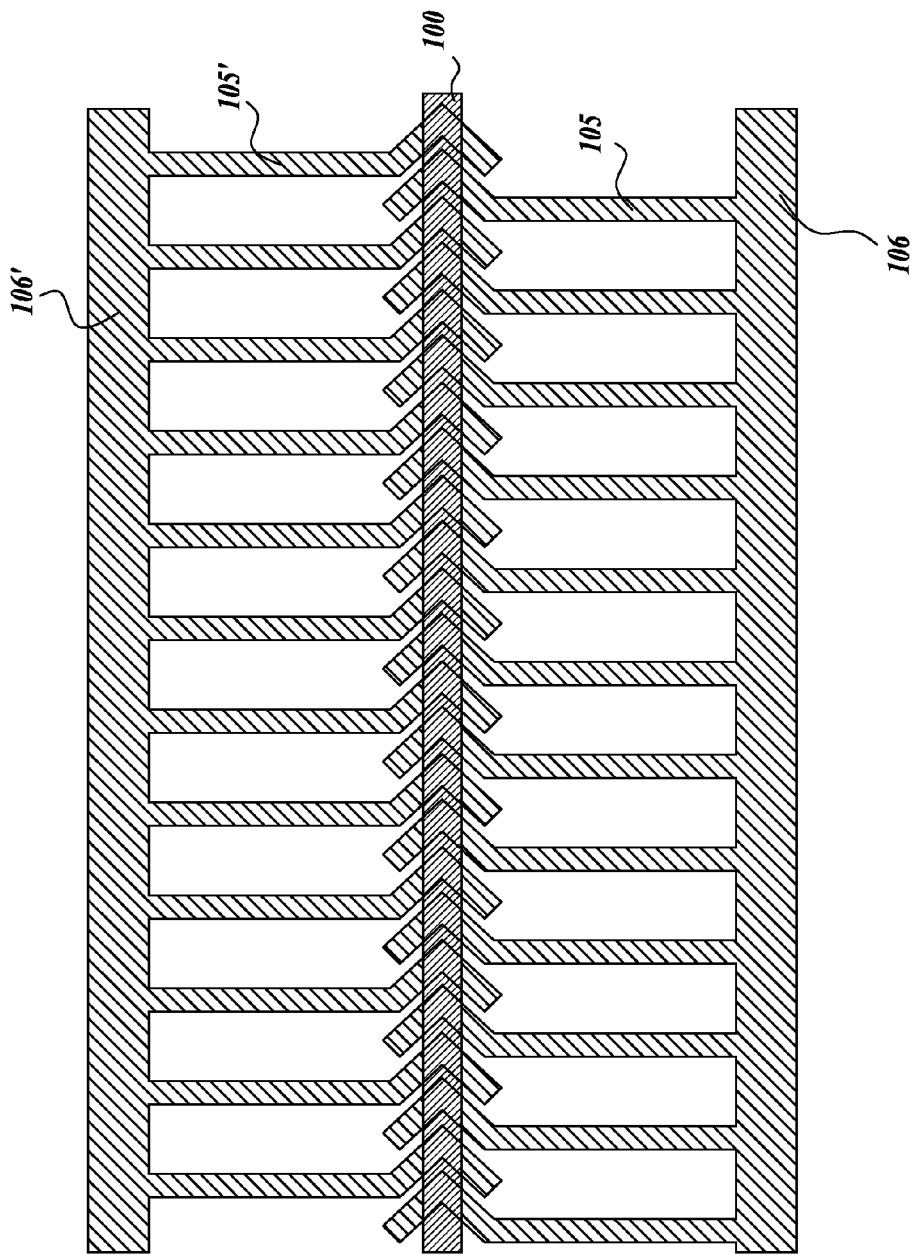
FIGS. 3A-3E illustrate representative electrode and channel configurations useful in devices in accordance with the present invention.
Figure 3C:
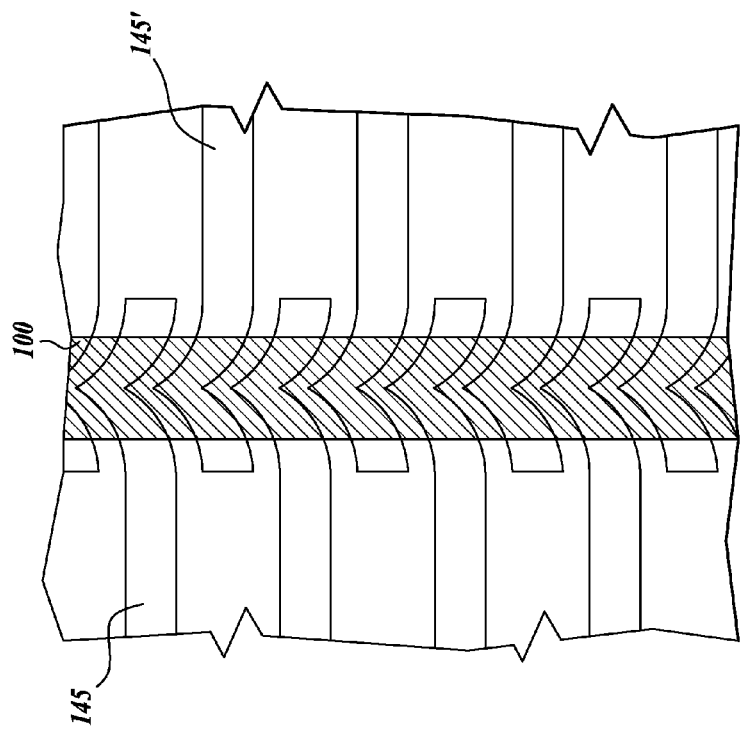
Figure 3B:
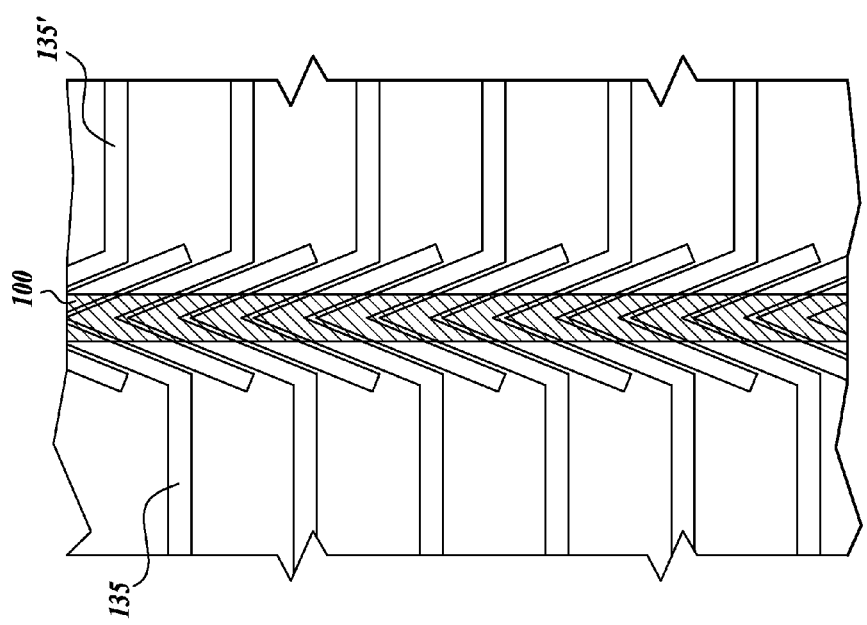
Figure 3E:
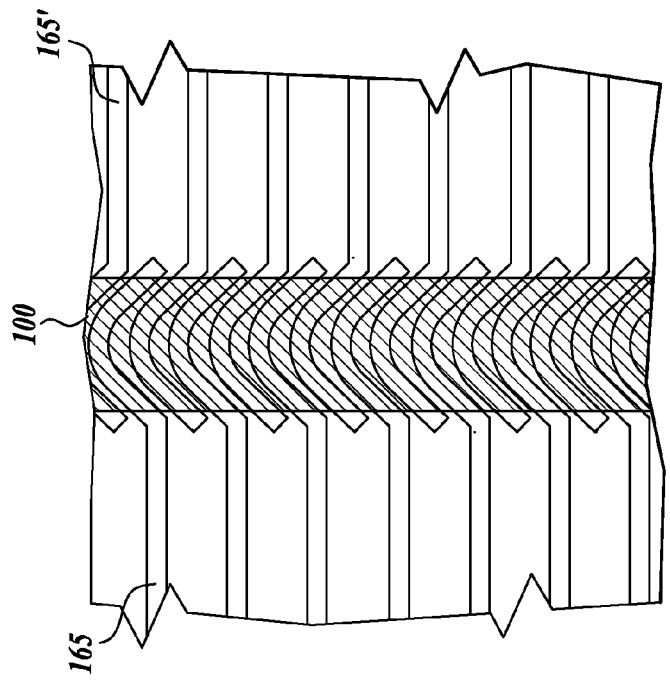
Figure 3D:
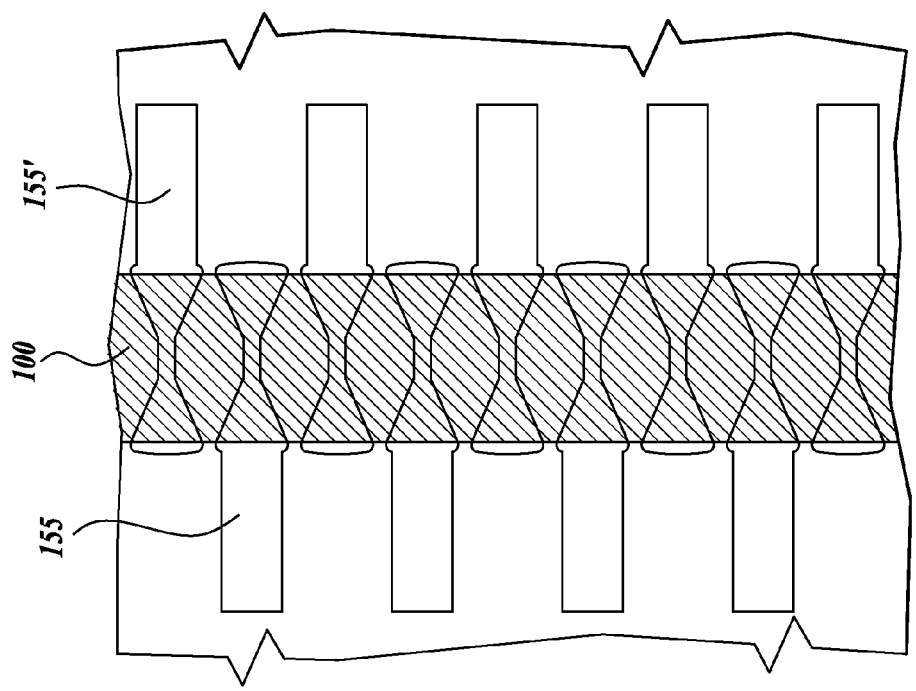

Alternative symmetric electrodes are illustrated in FIGS. 3B-3E. FIG. 3B illustrates steeply-angled V-shaped electrodes 135, 135', where the interior angle of the V-shape is less than 90 degrees. FIG. 3C illustrates non-linear V-shaped electrodes 145, 145'. Non-linear V-shaped electrodes 145, 145' generate a non-uniform electric field that is different from linear V-shaped electrodes 105, 105'. The curvature of the non-linear V-shaped electrodes 145, 145' can be optimized with respect to the hydrodynamic flow profile, flow rate, and DEP properties of the particles being separated in the channel 100. FIG. 3D illustrates bowtie-shaped electrodes 155, 155' having concave front and back profiles. Bowtie-shaped electrodes 155, 155' cause non-uniform DEP fields that have strong centering or anti-centering effects.

Bowtie-shaped electrodes can be combined with a V-shaped design to yield angled bowtie electrodes. FIG. 3E illustrates arcuate electrodes 165, 165'. These also create strong DEP centering or anti-centering effects, and the curvature can be varied to control the degree of "shunting," as previously described. Using angled bowtie electrodes, lateral movement due to DEP shunting can be made to compete with lateral movement from DEP forces due to the bowtie shape of the electrodes. For example, using positive DEP and flow from the legs to the tips of a V-shaped angled bowtie electrode, the shunting will move particles towards the center, but a competing DEP force from variation in the electric field across the channels can also pull particles towards the sides of the channel. In this manner, positive DEP moves some particles to the sides and others towards the center, without the need for negative DEP.

Additional arrays of electrodes can be disposed on the sides of the channel or the top or bottom of the channel.

Figure 4:
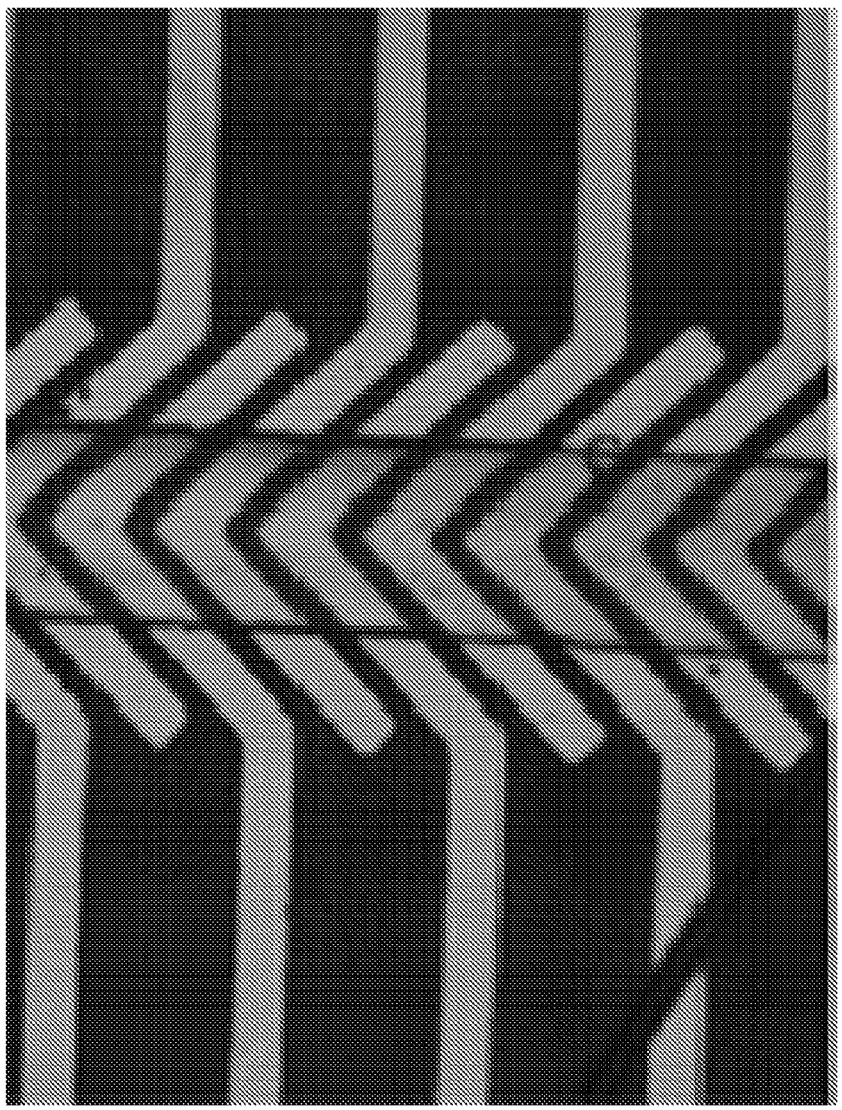
FIG. 4 is a micrograph of a representative device in accordance with the present invention.

A micrograph of a representative device is shown in FIG. 4. The device has metal electrodes that are V-shaped and deposited underneath a channel. The width of this exemplary channel is about 10 microns.

In the representative embodiment of FIG. 1A, the channel 100 is aligned with the interdigitated V-shaped electrodes 105, 105'. The region of the highest electric field gradient are along the edges of the V-shaped electrodes. In an exemplary embodiment DNA molecules of different lengths are sorted. For example, the particles 110, 112 may represent larger DNA particles 110 and smaller DNA particles 112. If particle 110 is more affected by positive DEP than particle 112 (because of a larger size) it will move in the direction of the flow and towards the edges of the channel 100 due to combined hydrodynamic and DEP forces. In this embodiment, particle 112 is not as affected by DEP as particle 110. The flow non-uniformity in the channel 100 (i.e., flow rate decreases from center of the channel towards the edge) causes the net distance traveled by the smaller DNA particle 112, that is less affected by DEP forces, to be greater than that of the longer DNA particle 110, that is more strongly affected by the DEP force, and thus moved closer to the edge of the channel. In this embodiment, if the flow were reversed, the opposite effect would occur: the particle 110 affected by positive-DEP would move towards the center of the channel 100.

It will be appreciated that the size, width, spacing, and number of electrodes in devices can be tailored for a specific liquid/particle system such that separation between multiple pluralities of disparate particles is maximized.

Device Operation

A means for introducing and flowing a liquid through a channel 100 is included. Liquid may be introduced to the channel 100 using fluidic vias to the channel, or through other on-chip channels or chambers used to inject liquid into the channel. Methods for creating liquid flow is known to those of skill in the art, and exemplary means for flowing a liquid include: pumps, pressure, and electro-osmotic flow. The liquid will typically contain the particles to be separated by the device when it is injected into the channel. Useful liquids are capable of containing particles to be separated.

As discussed above, when particles are laterally relocated in a channel by DEP, the difference in the hydrodynamic velocity near the sides versus the center of the channel 100 typically yields separation along the length of the channel through field-flow fractionation. Particles can be separated into distinct populations depending on their properties. The liquid 115 can be directed into multiple channels for analysis or analysis can be performed in the channel on the eluent as fractions of particles arrive at different times. Detection of particles is accomplished with techniques known to those of skill in the art. Exemplary means for detecting include: impedance sensing, methods using microscopy (e.g., fluorescence microscopy), assays, and integrated or partially integrated optical components (e.g., photodiodes, excitation/emission filters, and light-emitting diodes).

The signals applied to the electrodes for DEP are typically unsteady voltages, particularly AC signals greater than 3 kHz in frequency in order to avoid electrolysis while using high-voltage fields. Representative applied signals include sine, square, and triangle waves, and superpositions of these waves over a range of frequencies and amplitudes. Maximizing the DEP force on a specific particle population involves adjusting the composition of the applied electrical signals (and thus electric field in the channel), including pulsed waveforms and the duty cycle of the applied signal.

Figure 5B:
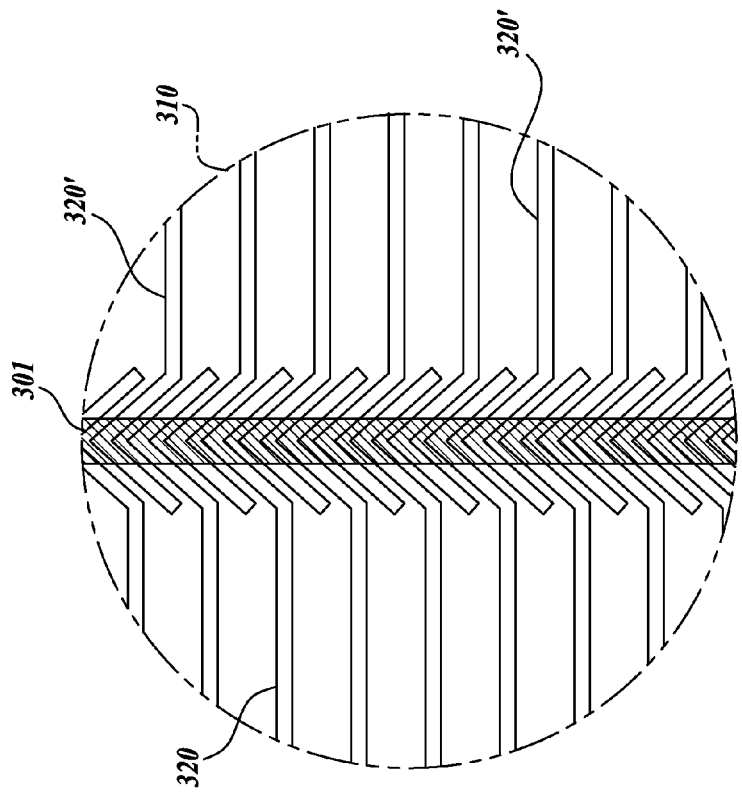
FIG. 5B is a close-up view of section 5B of the exemplary device shown in FIG. 5A.
Figure 5A:
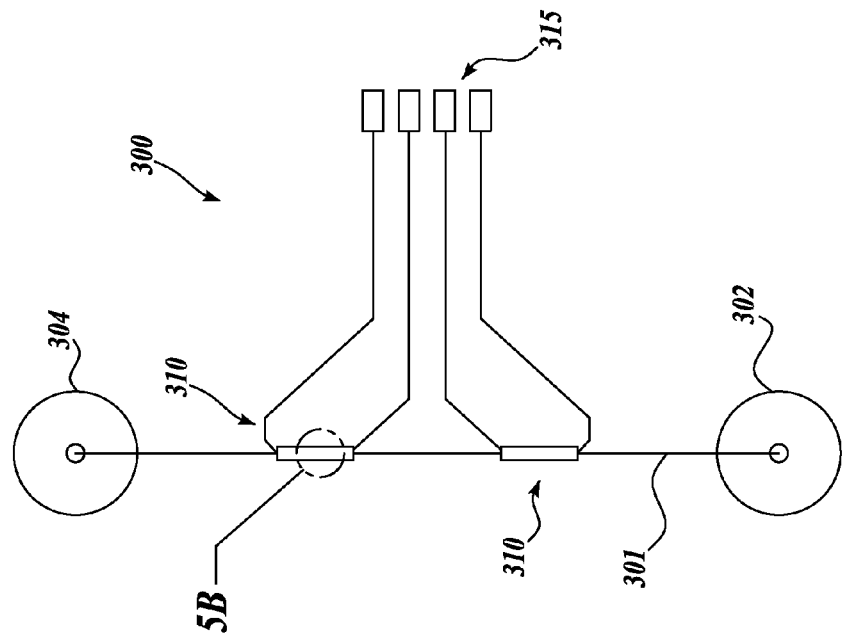
FIG. 5A is a sketch of an exemplary device in accordance with the present invention.

An exemplary device 300 is illustrated in plan view in FIG. 5A. A channel 301 runs longitudinally, having an inlet port 302, an outlet port 304, and two different regions of electrodes 310. The regions of electrodes 310 are connected to metal pads 315 for ease of operation. An enlarged view of a portion of the region 310 is illustrated in FIG. 5B, including the channel 301 and electrodes 320, 320'.

It is contemplated that electrode array configurations may vary over the length of the channel 301 (e.g., the angle forming the V-shape may change) or different configurations may be stacked sequentially (e.g., a V-shape followed by a bowtie configuration) in order to maximize separation performance. Another embodiment includes three-dimensional electrode configurations, where electrodes are patterned on the sides, top, or within the channel.

Figure 6:
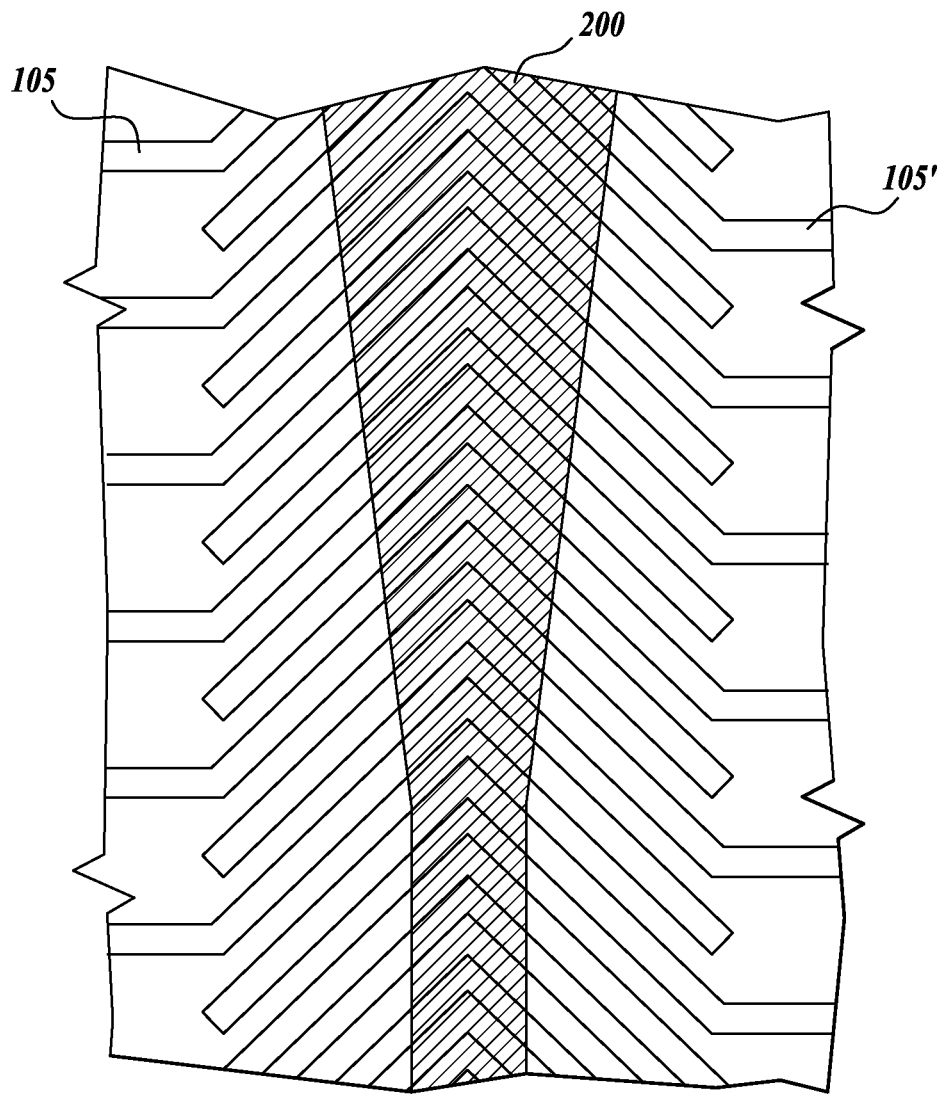
FIG. 6 illustrates a representative channel and electrode configuration useful in devices in accordance with the present invention.

The channel width and height can be varied. An increase in channel area (with constant flow rate) leads to a slower liquid velocity, such that the average amount that particles are affected by DEP can be slowly increased by gradually increasing the channel flow area. Similarly, a decrease in the channel area will increase the velocity in the channel and may increase the differential in downstream velocity for particles positioned in disparate locations within the cross-sectional area of the channel. Periodic narrowing and widening of the channel (having uniform height) may be combined with periodic electrode placement to maximize separation of particles. Variation in the width of a channel 200 is illustrated in plan view in FIG. 6. By varying the width of the channel 200, the devices may be tailored to optimize the effectiveness of DEP separations, as well as field-flow fractionation separations.

A representative device has microfluidic fittings as inlets and outlets for channels and a zero insertion force (ZIF) socket connected to the electrodes, which are typically photolithographically defined to interface properly with the channel. When a liquid containing particles is pushed from one microfluidic fitting through the channel to the other microfluidic fitting, the application of an electrical signal to the electrode arrays will cause DEP of particles susceptible to the force.

In an exemplary embodiment, fluorescent particles of disparate sizes are separated with DEP-FFF using concave electrodes (e.g., 105, 105', FIG. 3A) and imaged by optical fluorescence microscopy at the terminus of the channel 100. A 6 V (rms) 500 kHz signal applied to the electrodes 105, 105' yields the separation of 200 nm diameter fluorescent beads that are urged towards the edges of the channel by DEP forces, whereas 1-micron diameter fluorescent beads are moved towards the middle of the channel. As a result of field-flow fractionation, the 1-micron beads in the center of the channel flow faster than the beads at the edges and thus are detected before the 200 nm beads.

In a second exemplary embodiment, 46 kbp DNA suspended in a liquid is manipulated in a channel using V-shaped electrodes and a 5 V (rms), 1 MHz electrical signal applied across two interdigitated pluralities of electrodes disposed on the bottom of the channel. With a flow rate of 50 microns/second, the DNA is concentrated in the center of the channel when the flow of liquid is from the legs of the V-shaped electrodes towards the points, and the DNA is concentrated at the walls of the channel when the flow direction is reversed.

Device Fabrication

The fabrication of representative devices can be accomplished using well-known microfabrication techniques, such as photolithography, etching, and film deposition. It will be appreciated that the fabrication of electrodes and channels for use in microfluidic devices is well know to those of skill in the art and is not the focus of the present invention. The materials useful for fabricating devices are known to those of skill in the art and are limited only by the ability of the material to be processed according to the following procedure.

In an exemplary method, a substrate is used to fabricate the electrodes and electrode buses by, in sequence: photolithography, reactive ion etching, metallization, and photoresist lift off. The second wafer in this exemplary method is a glass superstrate processed by: plasma enhanced chemical vapor deposition (PECVD) of amorphous silicon ($\alpha$-Si); photolithography to define the shape of the channel; reactive ion etching of the $\alpha$-Si; and etching the glass with HF acid to complete the structure of the channel. Upon fabrication of the electrode wafer and the channel wafer, the two wafers are then interfaced so that the channel is aligned with the electrodes (disposed on the bottom surface of the channel) and electrode buses.

In a representative embodiment, the electrodes are V-shaped, arcuate, or bowtie-shaped electrodes. In this embodiment, the longitudinal direction of the channel is aligned with a line drawn through the points of the electrodes (the tips of the V-shaped or arcuate electrodes or the center of the bowtie-shaped electrodes). The amorphous silicon at the interface of the wafers facilitates anodic bonding and the two wafers are unified into a monolithic structure containing at least one device.

In one aspect, a system is provided having:

(a) an channel having a first side and a second side;

(b) an array of electrodes comprising a first plurality of electrodes extending into the channel and a second plurality of electrodes interdigitated with the first plurality of electrodes and extending into the channel, the first and second plurality of electrodes being disposed on the first side of the channel, and further wherein the electrodes are concave-shaped and substantially symmetric about a center line of the channel;

(c) an electrical power source operatively connected to the array of electrodes, and operable to apply a voltage to the first plurality and second plurality of electrodes such that the first plurality of electrodes is at a different electric potential than the second plurality of electrodes;

(d) a liquid having a plurality of disparate particles suspended therein; and (e) a means for flowing the liquid through the channel; such that the disparate particles suspended in the liquid are subjected to a non-uniform electrical field, thereby providing a lateral dielectrophoretic force on the disparate particles, wherein the particles are longitudinally separated by field-flow fractionation from the liquid lateral velocity profile.

Time-Varying Flow

Also provided are methods, devices, and systems that utilize time-varying flow of liquid in channels similar to those previously described.

In one aspect, a method is provided for spatially sorting particles using dielectrophoresis and field-flow fractionation comprising the steps:

providing a channel;

providing a first plurality of electrodes extending into the channel, and a second plurality of electrodes extending into the channel;

applying a first voltage to the first plurality of electrodes and a second voltage to the second plurality of electrodes such that the first plurality of electrodes is at a different electric potential than the second plurality of electrodes; and moving a liquid at a time-varying flow rate through the channel, the liquid having a first plurality of particles suspended therein and a second plurality of particles suspended therein, wherein the first plurality of particles and the second plurality of particles each have a property that affects dielectrophoretic forces induced by the applied first and second voltages, wherein the property is different in the first plurality of particles than in the second plurality of particles such that the first plurality of particles are urged laterally away from the second plurality of particles; thereby separating the first plurality of particles longitudinally from the second plurality of particles with field-flow fractionation from the liquid lateral velocity profile.

Time-varying or oscillating the flow of liquid 115 in the channel 100 enhances the potential number of velocity profiles 120 in the channel 100 without limiting the time liquid 115 spends in the region of the channel 100 near electrodes 105, 105'. Thus, by oscillating the flow of the liquid 115, particles (e.g., 110, 112) suspended therein can pass over the same electrodes 105, 105' several times, thereby being more strongly influenced by the DEP force.

In another aspect, a device is provided for spatially sorting particles suspended in a liquid, comprising:

(a) a channel;

(b) an array of electrodes comprising a first plurality of electrodes extending into the channel and a second plurality of electrodes extending into the channel;

(c) an electrical power source operatively connected to the array of electrodes, and operable to apply a first voltage to the first plurality of electrodes and a second voltage to the second plurality of electrodes such that the first plurality of electrodes is at a different electric potential than the second plurality of electrodes; and (d) a means for flowing a liquid through the channel in a time-varying manner, the liquid having a plurality of disparate particles suspended therein; such that the disparate particles suspended in the liquid are subjected to a non-uniform electrical field, thereby providing a lateral dielectrophoretic force on the disparate particles, wherein the disparate particles are laterally separated by the lateral dielectrophoretic force and longitudinally separated by field-flow fractionation from the liquid lateral velocity profile.

Means for generating a time-varying flow are known to those of skill in the art and include piezoelectric diaphragms and electromagnetic transducers (such as speaker drivers). Additional means include mechanical oscillators, circulating pumps, and rapid thermal cycling.

Referring again to FIG. 1, in an exemplary embodiment, a time-varying device can be fabricated with only one electrode array (consisting of two sets of interdigitated electrodes 105, 105'). By oscillating the flow of the liquid 115, particles 110, 112 in the liquid pass over the electrodes 105, 105' several times and are affected by a DEP force similar to that experienced by similar particles 110, 112 in a non-oscillating flow device that have passed over several hundred (or thousand) sets of electrode 105, 105'. As a result, oscillating-flow devices can greatly reduce the longitudinal channel 100 length required for separation of particles 110, 112. Devices having multiple arrays of electrodes increase the DEP force proportionately.

It will be appreciated that oscillating flow devices may have electrodes disposed on the top and/or bottom surface of the channel and need not be interdigitated.

Flow oscillations can be synchronized with the signal applied to the electrodes 105, 105' in the channel 100, typically through a synchronization of amplitude modulation of the applied waveform with the flow oscillations (e.g., the oscillation can be synchronized with the duty cycle of the signal). The flow can be completely oscillated in the channel 100 or the oscillation can be superimposed on a constant flow rate, thus creating a time-varying flow. The utility of oscillating flow used in combination with DEP-FFF devices is not limited to the concave-electrode devices previously described. However, representative methods and devices utilizing oscillating flow include DEP-FFF devices having concave electrodes 105, 105', including V-shaped 105, arcuate 165, and bowtie-shaped 155 electrodes.

The means for synchronizing the time-varying flow and the voltage applied to the electrodes 105, 105' can be accomplished by techniques known to those of skill in the art and include using the same voltage waveform, or transformation of a waveform, to actuate the electrodes 105, 105' and an electromechanical device used to generate the flow. An exemplary means for synchronizing the voltage and flow includes a clock or sync signal between electronic devices (or in a computer) that allows the signals sent for actuation of the transducer generating time-varying flow and the voltages for generating the DEP forces to be synchronized. Optimizing the phase difference between the time-periodic flow and DEP force can be determined experimentally for each device geometry.

In an exemplary embodiment, if the liquid 115 in the channel 100 is oscillated a distance of 250 μm at 100 Hz, a signal is applied to the electrodes 105, 105' that is multiplied by a square wave with a duty cycle of 100 Hz. In this embodiment, the square wave is synchronized with the flow oscillation such that the electric field is present when the flow is moving forward through the channel 100, and the field is absent when the flow is moving backward through the channel 100. Oscillating the liquid 115 can temporally vary DEP forces on a particle as a result of multiple passes across the electrodes 105, 105' (when an electric field is present), creating an effect as though the channel 100 were much longer.

The previous example can be extended to electric fields of different shapes synchronized with the forward periods and backward periods of the oscillations of the flow. For example, when the flow is moving backward, instead of removing the field, the field can be shaped to inhibit motion, for example, along the boundary of the channel.

In another aspect, a method is provided for spatially sorting particles using dielectrophoresis and field-flow fractionation using concave-shaped electrodes, comprising the steps:

providing a channel having a first side and a second side;

providing a first plurality of electrodes extending into the channel, and a second plurality of electrodes interdigitated with the first plurality of electrodes and extending into the channel, the first and second plurality of electrodes being disposed on one of the first side and the second side of the channel, wherein the electrodes are concave-shaped and substantially symmetric about a center line of the channel;

applying a voltage to the first plurality and second plurality of electrodes such that the first plurality of electrodes is at a different electric potential than the second plurality of electrodes; and moving a liquid at a time-varying flow rate, the liquid having a first plurality of particles suspended therein and a second plurality of particles suspended therein, through the channel, wherein the first plurality of particles and the second plurality of particles each have a property that affects induced dielectrophoretic forces, wherein the property is different in each of the pluralities of particles such that the first plurality of particles and the second plurality of particles become sorted by the property in a lateral direction as the liquid moves through the channel; thereby separating the sorted particles longitudinally with field-flow fractionation from the liquid lateral velocity profile.

In another aspect, a system is provided for spatially sorting particles suspended in a liquid, comprising (a) a channel;

(b) an array of electrodes comprising a first plurality of electrodes extending into the channel and a second plurality of electrodes extending into the channel;

(c) an electrical power source operatively connected to the array of electrodes, and operable to apply a voltage to the first plurality and second plurality of electrodes such that the first plurality of electrodes is at a different electric potential than the second plurality of electrodes; and (d) a liquid having a plurality of disparate particles suspended therein; and (e) a means for flowing the liquid through the channel in an time-variant manner; such that the disparate particles suspended in the liquid are subjected to a non-uniform electrical field, thereby providing a lateral dielectrophoretic force on the disparate particles, wherein the particles are longitudinally separated by field-flow fractionation from the liquid lateral velocity profile.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for spatially sorting particles using dielectrophoresis and field-flow fractionation comprising the steps:

providing a channel defining at least one electrode surface bordered laterally by a first sidewall and a second sidewall;

providing a first plurality of electrodes adjacent the electrode surface and extending along the electrode surface, and a second plurality of electrodes adjacent the electrode surface and extending along the electrode surface;

applying a first voltage to the first plurality of electrodes and a second voltage to the second plurality of electrodes such that the first plurality of electrodes is at a different electric potential than the second plurality of electrodes; and moving a liquid at an oscillating flow rate through the channel, the liquid having a first plurality of particles suspended therein and a second plurality of particles suspended therein, wherein the first plurality of particles and the second plurality of particles each have a property that affects dielectrophoretic forces induced by the applied first and second voltages, wherein the property is different in the first plurality of particles than in the second plurality of particles such that the first plurality of particles are urged laterally away from the second plurality of particles and towards at least one of the first sidewall and the second sidewall to an extent sufficient to reduce a flow rate of the first plurality of particles compared to a flow rate of the second plurality of particles according to a liquid velocity profile across a cross-section of the channel;

thereby separating the first plurality of particles longitudinally from the second plurality of particles with field-flow fractionation resulting from the liquid lateral velocity profile.

2. The method of claim 1, wherein the first plurality of electrodes and the second plurality of electrodes are concave-shaped and substantially symmetric about a center line of the channel.

3. The method of claim 2, wherein the first plurality of electrodes and the second plurality of electrodes are selected from the group consisting of V-shaped electrodes, arcuate electrodes, and bowtie-shaped electrodes.

4. The method of claim 1, wherein the first voltage and the second voltage are alternating voltages.

5. The method of claim 1, wherein the first voltage is applied intermittently to the first plurality of electrodes.

6. The method of claim 5, wherein the oscillating flow rate is synchronized with the intermittently applied first voltage.

7. The method of claim 6, wherein the intermittently applied first voltage is an alternating current having a duty cycle, and wherein the oscillating flow rate is synchronized with the alternating current by synchronizing the duty cycle with oscillations in the flow rate.

8. The method of claim 1, wherein the first plurality of particles and the second plurality of particles are independently selected from the group consisting of nucleic acids, cells, proteins, carbon nanotubes, and viruses.

9. The method of claim 8, wherein the first plurality of particles comprises strands of DNA having a first length, and the second plurality of particles comprises strands of DNA having a second length that is different from the first length.

10. The method of claim 1, further comprising a third plurality of electrodes disposed on a surface of the channel that is different than surfaces supporting the first and second pluralities of electrodes.

11. The method of claim 1, wherein the first plurality of electrodes and the second plurality of electrodes are separated from the channel by a protective layer.

12. The method of claim 1, wherein the first plurality of electrodes and the second plurality of electrodes are interdigitated.

* * * * *